US008940058B2

(12) United States Patent
Berte' et al.

(10) Patent No.: US 8,940,058 B2
(45) Date of Patent: Jan. 27, 2015

(54) FLUORESCENT WHITENING AGENT AQUEOUS SOLUTIONS

(75) Inventors: Ferruccio Berte', Bergamo BG (IT); Paolo Alioli, Bergamo BG (IT); Marco Brena, Bergamo BG (IT)

(73) Assignee: 3V Sigma S.p.A., Milan (IT)

( * ) Notice: Subject to any disclaimer, the term of this patent is extended or adjusted under 35 U.S.C. 154(b) by 0 days.

(21) Appl. No.: 14/235,344

(22) PCT Filed: Jul. 27, 2012

(86) PCT No.: PCT/IB2012/053855
§ 371 (c)(1),
(2), (4) Date: Apr. 2, 2014

(87) PCT Pub. No.: WO2013/018012
PCT Pub. Date: Feb. 7, 2013

(65) Prior Publication Data
US 2014/0203212 A1 Jul. 24, 2014

(30) Foreign Application Priority Data
Jul. 29, 2011 (IT) .............................. MI2011A1449

(51) Int. Cl.
D06L 3/12 (2006.01)
D06P 1/00 (2006.01)
C07D 251/70 (2006.01)
C11D 3/30 (2006.01)
C11D 3/42 (2006.01)
C11D 7/32 (2006.01)
D21H 21/30 (2006.01)
D21H 17/07 (2006.01)
C07D 251/18 (2006.01)
D21C 9/10 (2006.01)

(52) U.S. Cl.
CPC ............ *D06P 1/0012* (2013.01); *C07D 251/70* (2013.01); *C11D 3/30* (2013.01); *C11D 3/42* (2013.01); *C11D 7/3218* (2013.01); *D06L 3/12* (2013.01); *D21H 21/30* (2013.01); *D06L 3/1271* (2013.01); *D21H 17/07* (2013.01); *C07D 251/18* (2013.01); *D21C 9/1063* (2013.01)
USPC ....................................... 8/648; 8/654; 8/688

(58) Field of Classification Search
USPC ............................................ 8/648, 654, 688
See application file for complete search history.

(56) References Cited

U.S. PATENT DOCUMENTS 3,012,971 A 12/1961 Gessner et al.
4,497,718 A 2/1985 Neiditch et al.

FOREIGN PATENT DOCUMENTS

DE 1119646 12/1961
WO 2005/028749 3/2005
WO WO 2005/028749 A1 * 3/2005 ................ D06L 3/12

OTHER PUBLICATIONS

STIC Search Report dated Jun. 9, 2014.*
International Search Report issued in counterpart PCT Application No. PCT/IB2012/053855. (2012).
Written Opinion of International Searching Authority issued in counterpart PCT Application No. PCT/IB2012/053855. (2012).

* cited by examiner

*Primary Examiner* — Eisa Elhilo
(74) *Attorney, Agent, or Firm* — Silvia Salvadori, P.C.

(57) ABSTRACT

The present invention relates to a composition comprising a fluorescent whitening agent and a tertiary alkanolamine, a stable aqueous solution of such a composition and use of such composition for the bleaching of textile fibers or paper.

9 Claims, No Drawings

FLUORESCENT WHITENING AGENT AQUEOUS SOLUTIONS

CROSS-REFERENCE TO RELATED APPLICATIONS

This application is a 371 of PCT/IB2012/053855, filed Jul. 27, 2012, which claims the benefit of Italian Patent Application No. MI2011A001449, filed Jul. 29, 2011, the contents of each of which are incorporated herein by reference.

FIELD OF THE INVENTION

The present invention relates to a composition comprising a fluorescent whitening agent and a tertiary alkanolamine, a stable aqueous solution of such a composition and use of such composition for the bleaching of textile fibres or paper.

BACKGROUND OF THE INVENTION

The use of whitening agents to impart a higher degree of whiteness to goods such as paper, paperboard, textiles and nonwoven fabrics is well known. The most widely used whitening agents in the field of paper and cardboard are the derivatives of 4,4'-bis-[1,3,5-triazinyl]-diaminostilbene-2,2'-disulfonic acid substituted at the triazine ring with anilino and alkanolamino groups. The anilino groups may contain other sulfonic groups, but since these groups increase the solubility in water of the related molecules, they also reduce the affinity of the molecules towards the cellulose fibres that make up the paper so that they lead to inferior performance in terms of the degree of whiteness.

For reasons of ease of processing, the paper industry requires that these whitening agents are provided in the form of liquid fluid aqueous dispersions or, most preferably, of an aqueous solution stable for at least several months at temperatures from 5 to 40° C.

The stilbene whitening agents that are derivatives of 4,4'-bis-[1,3,5-triazinyl]-diaminostilbene-2,2'-disulfonic acid substituted at the triazine ring with anilino groups and alkanolamino groups, preferred in this field, are not readily soluble in water, hence the production of the relevant concentrated and stable aqueous solutions has required in the past the addition of significant amounts, even up to 30%, of solubilizing agents such as urea, caprolactame, ethylene glycol and polyglycols.

However, the added solubilizing agents does not have a great affinity for cellulose and do not contribute significantly to the performance of the product resulting in undesirable pollutants, at the end of the process of paper production. For example, in the case of use of whitening agents solutions formulated with urea, a strong additional polluting load consisting of nitrogen-based by-products and ammonia is introduced in the liquid effluents of the process.

A further problem derives from the inevitable presence in the whitening agents solutions of inorganic chlorides, for example sodium chloride, which is derived from the synthesis processes of the whitening agents. In fact, all the industrial processes of production of stilbene whitening agents substituted with triazine involve the use of cyanuric chloride as a reagent, which reacts in successive stages with different required amino products inevitably leads to generation of large quantities of inorganic chlorides that are difficult to eliminate.

The remaining inorganic chlorides generate instability in aqueous whitening agents concentrated solutions so that it is essential to significantly reduce the content thereof, inevitably using costly osmotic separation techniques, to obtain compositions that remain stable for a long time.

U.S. Pat. No. 3,012,971 discloses compositions for the bleaching of paper formed of concentrated aqueous solutions of 4,4'-bis-[2-phenylamino-4-diethanolamino-1,3,5-triazinyl]-diaminostilbene-2,2'-disulfonic acid or a salt thereof in admixture with alkanolamines, wherein the proportion by weight of alkanolamines with respect to the whitening agents varies from 0.5:1 to 3.0:1. Since the molecular weight of alkanolamines is much lower than that of the whitening agents, said range defines a large excess of alkanolamine compared to the whitening agent. However, such high amounts of alkanolamines, compared to the whitening power of the composition, are not acceptable from the ecological point of view.

WO 2005/028749 discloses aqueous compositions comprising stilbene whitening agents and alkanolamines. This document does not describe any example of a composition comprising a tertiary alkanolamine. In addition, there is no mention of the problem of the effect of inorganic chlorides on the stability of the solution.

U.S. 2010/0159763 describes aqueous compositions of fluorescent whitening agents, substituted to the triazine rings with propionamide amino groups, having the following formula:

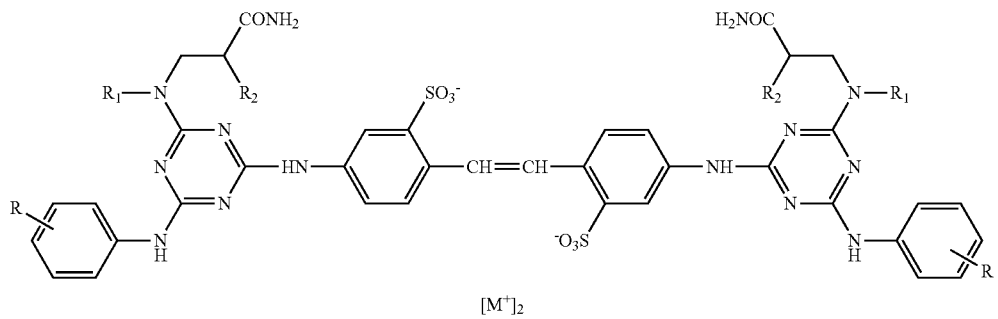

$[M^+]_2$ wherein at least 25% of the $[M^+]$ ions associated with the sulfonic group have been replaced by $(CH_3)_2NH^+CH_2CH_2OH$ ions. However, in order to guaranteeing the stability of the formulation, it is necessary in such compositions to reduce the content of inorganic salts by suitable osmosis processes.

IT 1356016 discloses a method for the optical whitening of the paper through the use of substantially aqueous suspension of the compound having the following formula:

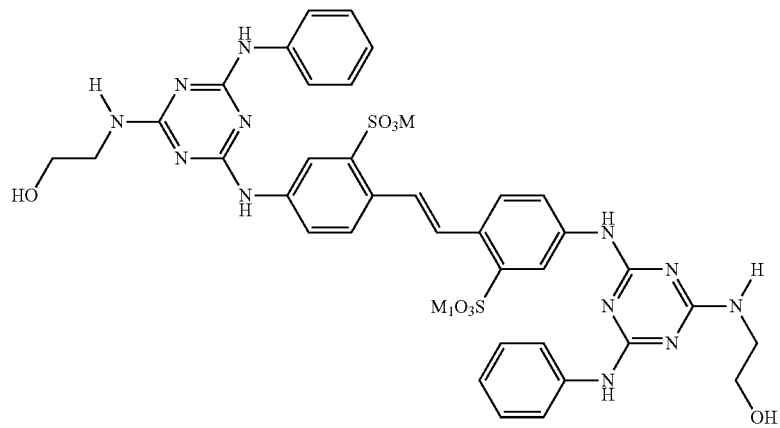

wherein M and $M_1$ represent hydrogen, an alkali metal, an alkaline earth metal or ammonium.

SUMMARY OF THE INVENTION

Therefore, object of the present invention is to provide a composition of whitening agents which is stable in aqueous solution, even in the presence of small amounts of inorganic chlorides normally remaining at the end of the synthesis and without the addition of stabilizing additives or solubilizers.

Said object is achieved with a composition, a compound, an aqueous solution and a method of use whose main features are specified in the appended claims.

DETAILED DESCRIPTION OF THE INVENTION

Surprisingly, it has now been discovered that aqueous solutions and/or compositions in the form of concentrated aqueous solution of some fluorescent whitening agents and a particular tertiary alkanolamines, are stable even in the presence of significant amounts of salts and in particular of sodium chloride. These solutions are stable regardless of the presence of suitable stabilizers or solubilizers.

This property allows the production process to be simplified, by avoiding the introduction of the steps of final purification of the whitening agent from the salts, such as by osmosis.

The compositions according to the present invention include:

i) at least one compound of formula (I): $NR_1R_2R_3$, wherein $R_1$, $R_2$ and $R_3$ are selected in the group consisting of linear or branched $C_1$-$C_6$ alkyl groups, $C_3$-$C_6$ cycloalkyl groups, linear or branched $C_1$-$C_6$ hydroxyalkyl groups, $C_3$-$C_6$ hydroxycycloalkyl groups; and wherein at least one of $R_1$, $R_2$ and $R_3$ is a linear or branched $C_1$-$C_6$ hydroxyalkyl group; and ii) at least one compound of formula (II):

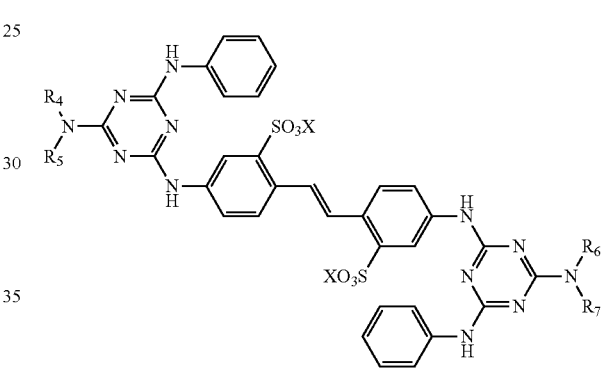

wherein $R_4$, $R_5$, $R_6$, $R_7$, each independently of the others, are selected in the group consisting of H, linear or branched $C_1$-$C_6$ alkyl groups, $C_3$-$C_6$ cycloalkyl groups, linear or branched $C_1$-$C_6$ hydroxyalkyl groups, $C_3$-$C_6$ hydroxycycloalkyl groups; and X is selected in the group consisting of hydrogen, alkali metals, alkaline earth metals, ammonium or ammonium derived from a compound of formula (I).

As examples of groups $R_1$, $R_2$ and $R_3$ may be mentioned methyl, ethyl, propyl, isopropyl, n-butyl, isobutyl, sec-butyl, tert-butyl, n-pentyl, iso-pentyl, neopentyl, hexyl, cyclopentyl, cyclohexyl, hydroxyethyl, hydroxypropyl, hydroxybutyl.

As examples of groups $R_4$, $R_5$, $R_6$ and $R_7$ may be mentioned hydrogen, methyl, ethyl, propyl, isopropyl, n-butyl, isobutyl, sec-butyl, tert-butyl, n-pentyl, iso-pentyl, neopentyl, hexyl, cyclopentyl, cyclohexyl, hydroxyethyl, hydroxypropyl, 2-hydroxypropyl, 3-hydroxypropyl, hydroxybutyl.

Preferably, the compound of formula (I) contained in the composition according to the present invention is an ethanolamine, wherein $R_1$ and $R_2$ are selected in the group consisting of $C_1$-$C_3$ alkyl groups and $R_3$ is a hydroxyethyl group.

Even more preferably, the composition according to the present invention comprises a compound of formula (I) consisting of 2-(dimethylamino)ethanol.

The whitening agents of formula (II) contained in the composition according to the present invention are preferably selected in the group consisting of the following compounds of formula (IIa), (IIb), (IIc), (IId), (IIe), (IIf):

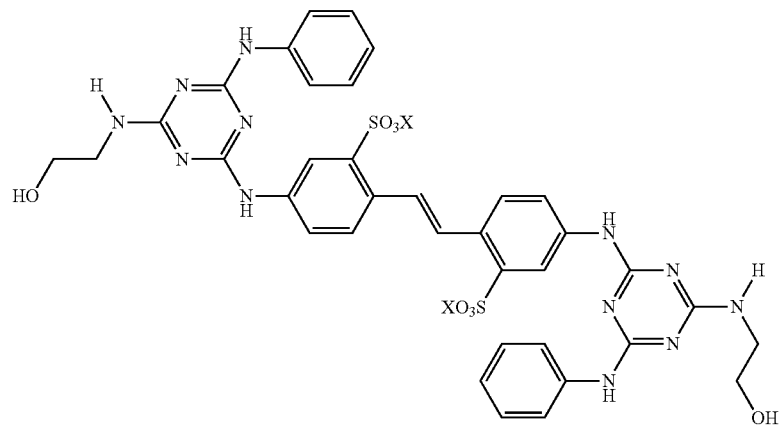
formula (IIa)
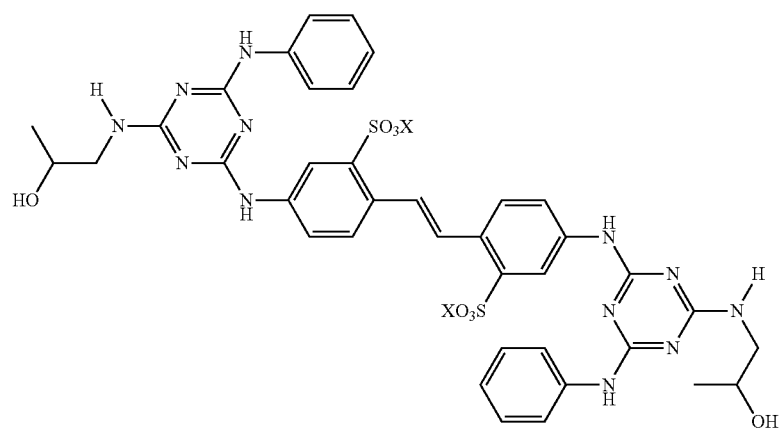
formula (IIb)
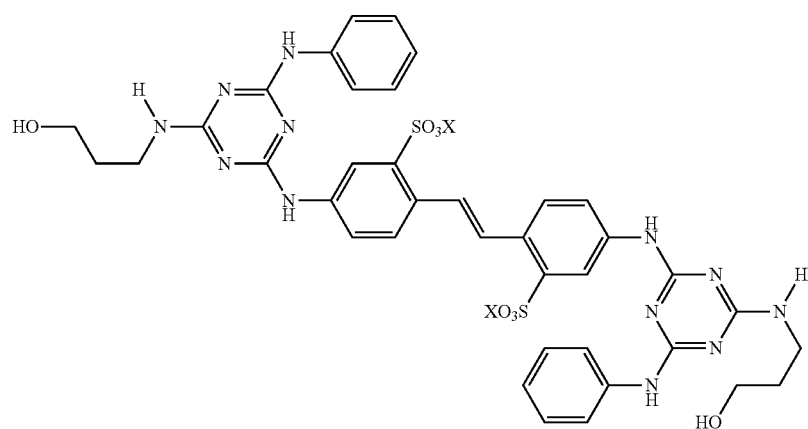
formula (IIc)

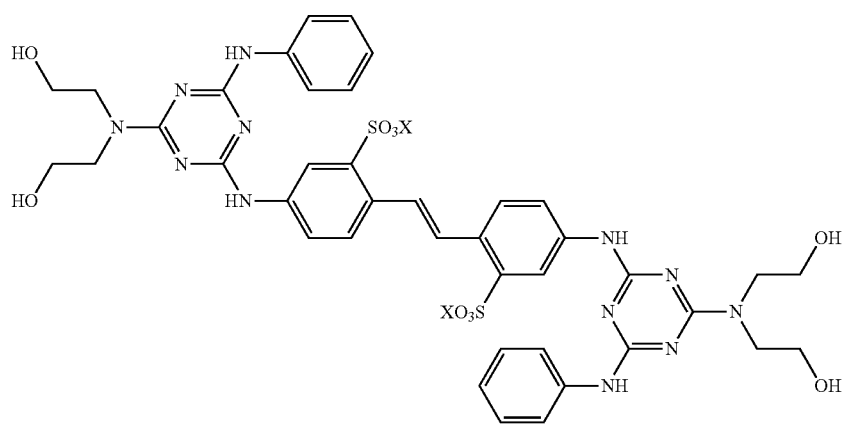

Formula (IId)

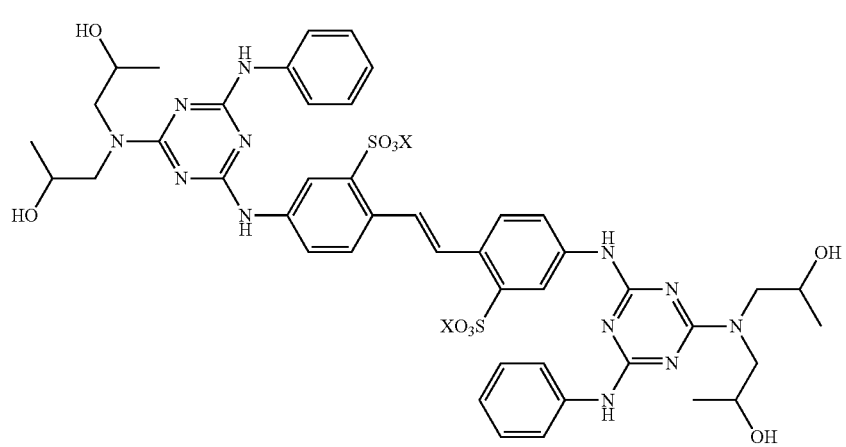

Formula (IIe)

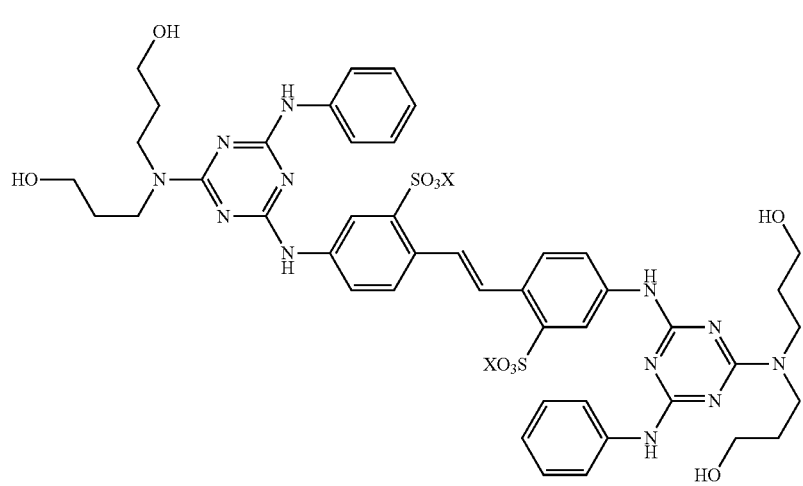

Formula (IIf)

in which X is as defined above.

The ratio between the quantity in moles of the compound of formula (I) and the compound of formula (II) in the composition according to the invention is preferably less than 3. More preferably, this ratio is less than 2.5.

The compounds of formula (II) wherein X is an ammonium ion derived from a compound of formula (I) are innovative fluorescent whitening agents whose stability in aqueous solution is particularly advantageous with respect to the compounds known in the art.

Therefore, in a further aspect, the invention concerns a compound derived from the salification of a whitening agent of formula (II) with an alkanolamine of formula (I). This compound according to the present invention is represented by the general formula (III)

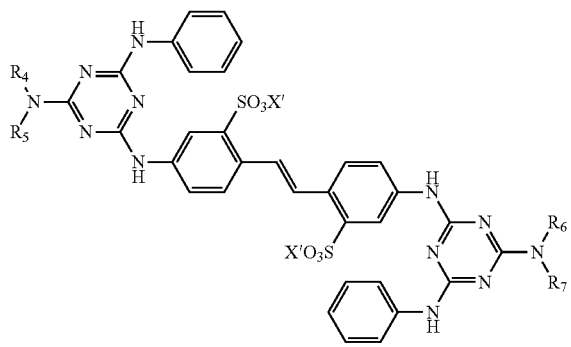

formula (III)

wherein X' is an ammonium ion derived from a compound of formula (I) defined in claim 1 and $R_4$, $R_5$, $R_6$, $R_7$ are as defined in claim 1.

Preferably, X' is an ammonium ion derived from a compound of formula (I), wherein $R_1$ and $R_2$ are selected from the group consisting of $C_1$-$C_3$ alkyl groups and $R_3$ is a hydroxyethyl group. Even more preferably, X' is an ammonium ion derived from 2-(dimethylamino)ethanol.

Particularly advantageous proved to be compounds selected in the group consisting of the following formulas (IIIa), (IIIb), (IIIc), (IIId), (IIIe), (IIIf):

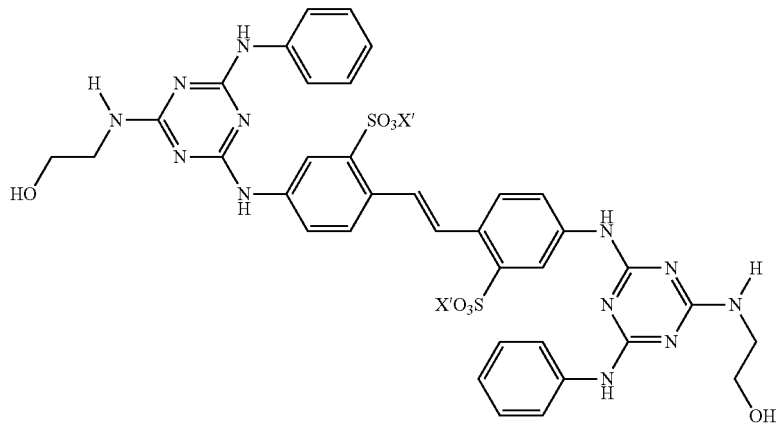

formula (IIIa)

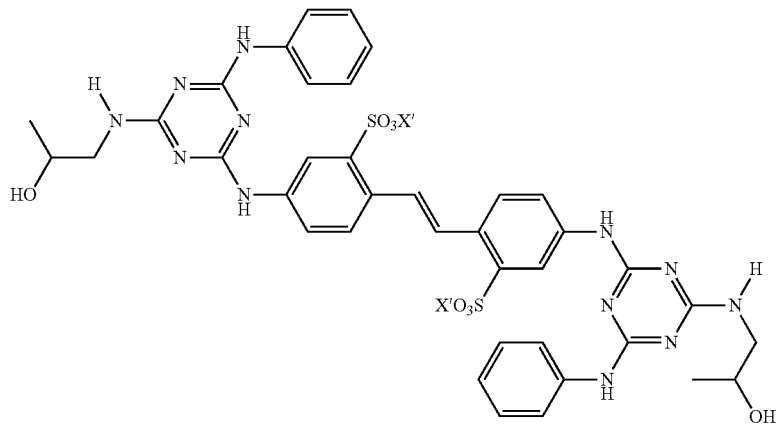

formula (IIIb)

-continued
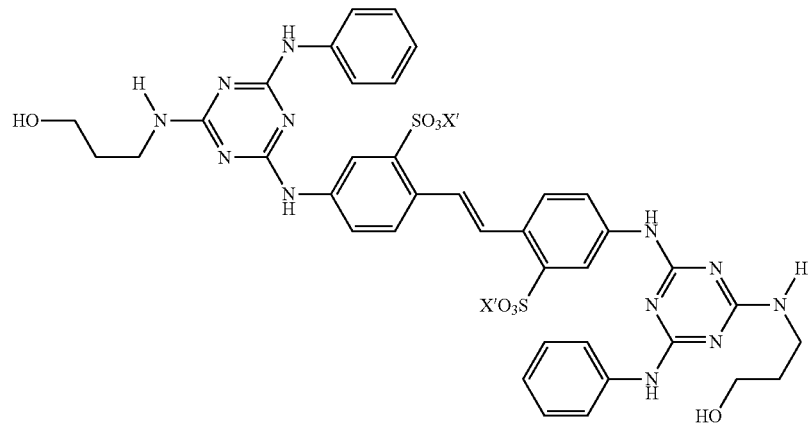
formula (IIIc)
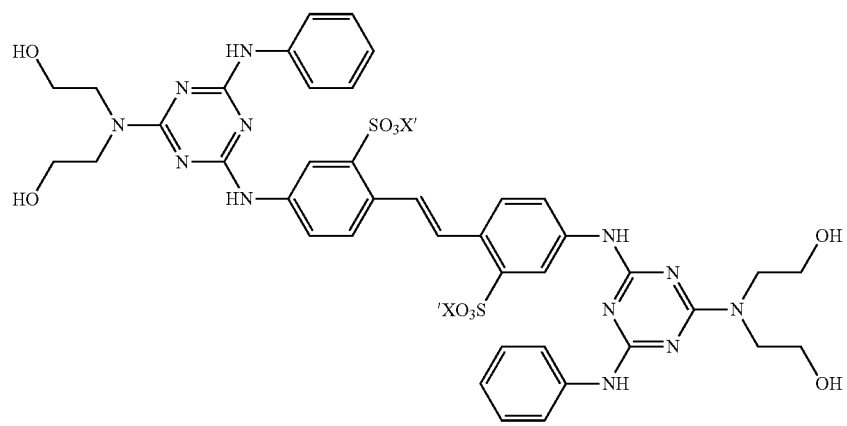
formula (IIId)
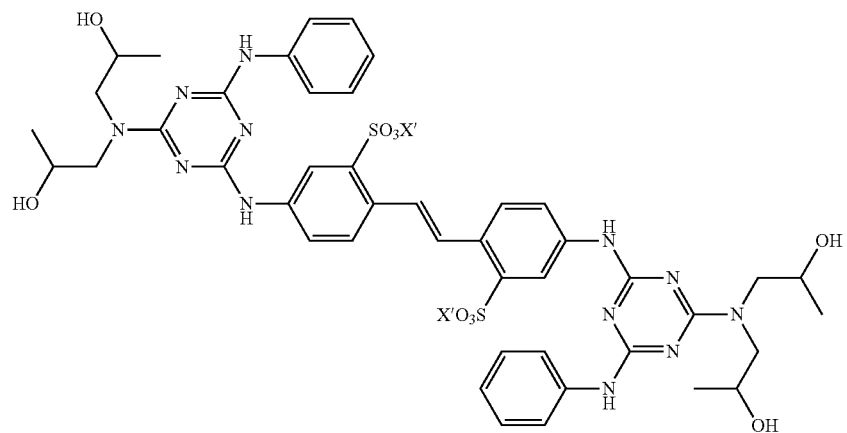
formula (IIIe)

formula (IIIf)

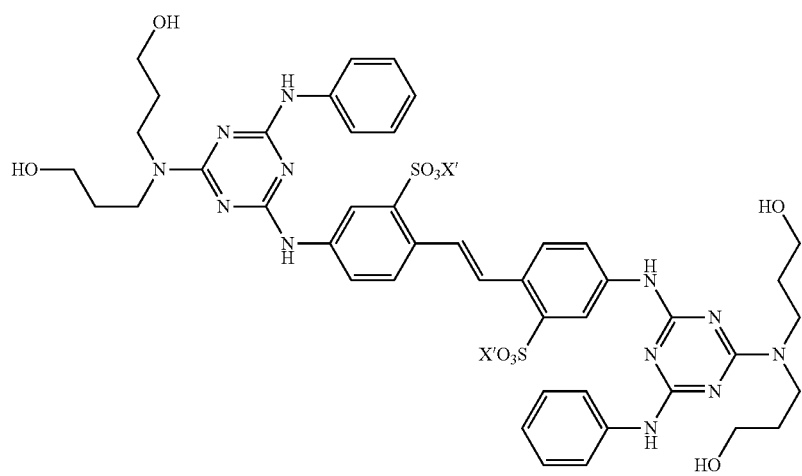

wherein group X' is an ammonium ion derived from 2-(dimethylamino)ethanol.

For these compounds, stability in aqueous solution at temperatures from 5° C. to 40° C. and in the presence of high amounts of sodium chloride has been confirmed, for example amounts of sodium chloride of about 1% by weight on the total weight of the solution.

Such compounds can be prepared by processes comprising the following steps:
mixing a compound of formula (II) with a compound of formula (I) in a suitable solvent medium, and
reacting at a temperature between 20° C. and 100° C.

In a further aspect, the invention relates to a concentrated aqueous solution comprising:
from 3% to 20% by weight of at least one compound of formula (I) as above defined or mixtures thereof;
from 6% to 40% by weight of at least one compound of formula (II) as above defined or mixtures thereof;
from 50% to 90% by weight of water; and
from 0% to 1% by weight of additives.

Therefore, the aqueous solution according to the present invention may comprise only a slight excess of alkanolamine of formula (I) with respect to the fluorescent whitening agent of formula (II) so that it is compatible with the current ecological regulations; it is stable for a long time even in the absence stabilizing agents and also in the presence of any inorganic chlorides arising from the production process of the whitening agent.

The aqueous solutions according to the present invention may, however, comprise further components such as additional whitening agents, inorganic salts, surfactants, preservatives, solubilizing agents or organic solvents.

Examples of whitening agents used in the aqueous solution according to the present invention are the stilbene tetra and/or hexasulfonated whitening agents.

Examples of inorganic salts usable in the aqueous solution according to the present invention are sodium sulfate, ammonium chloride and potassium chloride.

Examples of surfactants usable in the aqueous solution according to the present invention are polynaphtalenesulphonates, ethoxylated fatty alcohols.

Examples of preservatives used in the aqueous solution according to the present invention are glutaraldehyde, the isothiazolinones, 2-bromo-2-nitropropane-1,3-diol.

Examples of solubilizing agents usable in the aqueous solution according to the present invention are polyethylene glycols, urea, caprolactam.

Examples of organic solvents usable in the aqueous solution according to the present invention are ethylene and propylene glycols and the $C_1$-$C_4$ alkyl ethers thereof.

The solutions according to the present invention are obtained by dissolving the fluorescent agent of formula (II) in water or in a mixture of water and another solvent miscible with water, then adding the compound of formula (I), possibly while heating and stirring the solution.

The solutions according to the invention can be used for the whitening of natural, synthetic or semi-synthetic fibres, or of paper.

In particular, during the manufacture of paper, optical brighteners according to the present invention can be used either by adding them to the dispersion of fibres, which is generally known as pulp, or through size-press or coating surface treatments.

The invention will be illustrated in the following with reference to the following non-limiting examples.

The whitening agents described in the present invention were practically evaluated by coating, which consists in surface application of one or several uniform layers of compositions essentially comprising a mineral pigment and an adhesive (binder) on the surface of the sheet.

In all the examples of application, the coated samples were obtained by applying, by means of laboratory doctor blade, a uniform layer of a coating prepared according to the following recipe: (standard coating)
80 parts of Hydrocarb 90AV calcium carbonate
20 parts of Hydrafine kaolin
12 parts of Stironal D517 synthetic binder
0.5 parts of Finnfix 10 carboxymethyl cellulose
Sodium hydroxide solution (10% NaOH) to pH ~9
Demineralized water up to the final dry content of 65%.

The support paper used in all the examples of application was the type "Fabriano liscio 2" having grammage of 110 g/m².

At the end of the application the samples were dried at room temperature for one hour.

The degree of whiteness was detected by a Elrepho Datacolor LWE450-X reflectometer.

The thus prepared standard coating was applied as such on paper support to produce a reference degree of whiteness (fluorescent whitening agent dose=0):

| | Dosage FWA | D65/10° Brightness | D65/10° CIE Whiteness |
|---|---|---|---|
| reference whiteness degree | 0.0% | 88.1 | 80.07 |

Subsequently, the standard coating was additioned with 1.40% by weight of fluorescent whitening agents formulated to E11=105, then it was applied on the support; the yield of application of the whitening agents can be quantified by the increase in degree of whiteness of the paper after application in comparison with the of reference whiteness degree.

The values obtained are reported in Table 1.

In all examples, the extinction was measured by UV-VIS spectrophotometer Perkin-Elmer Lamda with an optical path of 1 cm.

The value of sodium chloride was determined by titrating the chloride ions with Mettler automatic titrator with silver nitrate 0.1 M.

EXAMPLE 1

570 g of an aqueous solution containing about 131.5 g (0.1599 moles) of the compound having the following formula (IV)

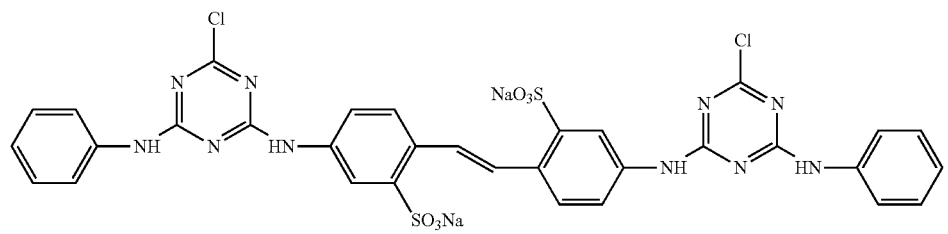

formula (IV)

were additioned simultaneously with 27 g of 80% monoethanolamine (0.3538 moles) dissolved in 169 g of demineralized water and 44.2 g (0.3317 moles) of 30% NaOH, by maintaining the temperature between 80 and 95° C. and the pH between 8.5 and 9.5. The addition was carried out in 30 minutes. After three hours at 95° C., stirring was interrupted, the reaction mixture was allowed to cool and the lower organic phase was separated from the upper aqueous phase.

To 290 g of organic phase about 500.0 g of demineralized water were added, the mixture was heated up to 65° C. and 30.6 g of 37% HCl and immediately afterwards 71 g of triethanolamine (0.4765 moles) were added. The temperature was maintained at 65-70° C. under stirring until the solid was transformed in an organic oily phase.

Subsequently, the stirring was interrupted, it was cooled to 20-30° C. and two phases separated.

About 400 g of demineralized water were added to 380 g of organic phase. It was clarified with earth filter, thus obtaining about 780 g of solution.

The concentration of the solution was determined as 21% and contained about 163 g (0.1450 moles) of the compound of formula (Ma) in which X'=HN$^+$(CH$_2$CH$_2$OH)$_3$. The solution was determined to have an extinction value E11 of about 105, and a NaCl content of about 0.54% by weight.

Portions of this solution were subjected to stability tests at 5° C., 20° C. and 40° C. This solution showed to be unstable at all temperatures and generated after 4 days a crystalline sediment at 20° C. and 40° C. At 5° C. a crystalline sediment was generated after 6 days.

Evaluation in coating E11 105; FWA in the coating: 1.4%
D65 brightness: 96.3
D65 CIE whiteness: 102.14

EXAMPLE 2

570 g of an aqueous solution containing about 131.5 g (0.1599 moles) of the compound having the above formula (IV) were additioned simultaneously with 27 g of 80% monoethanolamine (0.3538 moles) in a solution of 169 g of demineralized water and 44.2 g (0.3317 moles) of 30% NaOH.

The addition was carried out at a temperature of 80-95° C. and by maintaining the pH between 8.5 and 9.5. After three hours at 95° C., the stirring was interrupted, reaction mixture was allowed to cool and the lower organic phase was separated from the upper aqueous phase.

To 290 g of organic phase, about 500.0 g of demineralized water were added, the mixture was heated up to 65° C. and 30.6 g of 37% HCl and, immediately afterwards, 71 g of triethanolamine (0.4765 moles) were added. The temperature was maintained, under stirring, until the solid was transformed in an organic oily phase.

Subsequently, the stirring was interrupted, it was cooled to 20-30° C. and two phases separated.

About 400 g of demineralized water were added to 380 g of organic phase. It was clarified with earth filter, thus obtaining about 780 g of solution, which were determined to have a value of E11 of about 105, and a NaCl content of about 0.6% by weight.

To the clarified solution were added 380 ml of demineralized water with osmosis module OSMONIC mod SY-SEPA CF. 600 grams of salt water were removed, thus obtaining 560 of concentrated solution. By dilution with 220 ml of demineralized water, about 780 g of 20% solution which contained about 156 g (0.1387 moles) of the compound of formula (Ma) in which X'=HN$^+$(CH$_2$CH$_2$OH)$_3$ were obtained.

The solution was determined to have an extinction value of E11 of about 105 and a content of NaCl of about 0.15%.

Portions of this solution were subjected to stability tests at 5° C., 20° C. and 40° C. The solution was stable for one month at such temperatures.

Evaluation in coating E11 105; FWA in the coating: 1.4%
D65 brightness: 96.0
D65 CIE whiteness: 101.64

EXAMPLE 3

570 g of an aqueous solution containing about 131.5 g (0.1599 moles) of the compound having the above formula (IV) were additioned simultaneously with 27 g of 80% monoethanolamine (0.3538 moles) in a solution of 169 g of demineralized water and 44.2 g (0.3317 moles) of 30% NaOH.

The addition was carried out at a temperature of 80-95° C. and by maintaining the pH between 8.5 and 9.5. After three hours at 95° C., the stirring was interrupted, reaction mixture was allowed to cool and the lower organic phase was separated from the upper aqueous phase.

To 290 g of organic phase, about 500.0 g of demineralized water were added, the mixture was heated up to 65° C. and 30.6 g of 37% HCl and, immediately afterwards, 42.6 g of 2-(dimethylamino)ethanol (0.4786 mol) were added. The temperature was maintained, under stirring, until the solid was transformed in an organic oily phase.

Subsequently, the stirring was interrupted, it was cooled to 20-30° C. and two phases separated.

About 400 g of demineralized water were added to 360 g of organic phase. It was clarified with earth filter, thus obtaining about 760 g of 20% solution, which contained about 152 g (0.1513 moles) of the compound of formula (IIIa) wherein $X'=(CH_3)_2N^+(CH_2CH_2OH)$. The solution was determined to have a value of E11 of about 105, and a NaCl content of about 0.52% by weight.

The solution was determined to have an extinction value of E11 of about 105 and a content of NaCl of about 0.15%.

Portions of this solution were subjected to stability tests at 5° C., 20° C. and 40° C. The solution was stable for one month at such temperatures.

Evaluation in coating E11 105; FWA in the coating: 1.4%

D65 brightness: 96.2

D65 CIE whiteness: 102.30

EXAMPLE 4

570 g of an aqueous solution containing about 131.5 g (0.1599 moles) of the above compound of formula (IV) were additioned simultaneously with 37 g of diethanolamine (0.3538 mol) dissolved in a solution of 159 g of demineralized water and 44.2 g (0.3317 moles) of 30% NaOH.

The addition was carried out at a temperature of 80-95° C. and by maintaining the pH between 8.5 and 9.5. After three hours at 95° C., stirring was interrupted, it was allowed to cool and the lower organic phase was separated from the upper aqueous phase.

About 500.0 g of demineralized water were added to 305 g of organic phase, the mixture was heated to 65° C. and 30.6 g of 37% HCl and, immediately afterwards, 71 g of triethanolamine (0.4786 moles) were added. The temperature was kept under stirring until the transformation of the solid in an organic phase oily was complete.

Subsequently, the stirring was interrupted, it was cooled to 20-30° C. and two phases separated.

About 400 g of organic phase were added to 395 g of demineralized water and heated to 45-50° C., thus obtaining a slurry that was not filterable with decolorizing earth and having a NaCl content of 0.50%.

Therefore, aqueous solutions of compound (Ma) in which $V=HN^+(CH_2CH_2OH)_3$ are not obtainable using a molar ratio of the alkanolamine reagent to the whitening agent equal to 3.

EXAMPLE 5

570 g of an aqueous solution containing about 131.5 g (0.1599 moles) of the above compound of formula (IV) were additioned with 37 g of diethanolamine (0.3538 mol) dissolved in a solution of 159 g of demineralized water and, simultaneously, with 44.2 g (0.3317 moles) of 30% soda.

The addition was carried out at a temperature of 80-95° C. and by maintaining the pH between 8.5 and 9.5. After three hours at 95° C., stirring was interrupted, the solution was allowed to cool and the lower organic phase was separated from the upper aqueous phase.

About 500.0 g of demineralized water were added to 305 g of organic phase, the mixture was heated to 65° C. and 30.6 g of 37% HCl and, immediately afterwards, 42.6 g of dimethylethanolamine (0, 4786 moles) were added. The temperature was kept under stirring until the transformation of the solid in an organic phase oily was complete.

Subsequently, the stirring was interrupted, it was cooled to 20-30° C. and two phases separated.

About 400 g of demineralized water were added to 375 g of organic phase. It was clarified with earth filter, thus obtaining about 775 g of 20% solution which contained about 155 g (0.1416 moles) of the compound of formula (IIId) in which $X'=(CH_3)_2NH^+(CH_2CH_2OH)$.

The solution was determined to have an extinction value of E11 of about 105 and a NaCl content of about 0.45% by weight.

Portions of this solution were subjected to stability tests at 5° C., 20° C. and 40° C. The solution was stable for one month at such temperatures.

Thus, surprisingly it is possible to produce aqueous solutions of compound (IIId) using a molar ratio of alkanolamine reagent to whitening agent equal to 3.

Evaluation in coating E11 105; FWA in the coating: 1.4%
D65 brightness: 96.5
D65 CIE whiteness: 101.61

The results of the tests given above are summarized in the following Tables 1 and 2.

TABLE 1

| Sample | FWA Dosage | D65/10° Brightness | D65/10° CIE Whiteness Value | Increase |
|---|---|---|---|---|
| Reference whiteness grade | 0.0% | 88.1 | 80.07 | |
| Example 1 | 1.40% | 96.3 | 102.14 | +22.07 |
| Example 2 | 1.40% | 96.0 | 101.64 | +21.57 |
| Example 3 | 1.40% | 96.2 | 102.30 | +22.23 |
| Example 5 | 1.40% | 96.5 | 101.61 | +21.54 |

TABLE 2

| Example | $R_4, R_6$ | $R_5, R_7$ | X' | % NaCl | Stability |
|---|---|---|---|---|---|
| 1 | H | —$CH_2CH_2OH$ | $N(CH_2CH_2OH)_3$ | 0.54 | separation |
| 2 | H | —$CH_2CH_2OH$ | $N(CH_2CH_2OH)_3$ | 0.15 | stable |
| 3 | H | —$CH_2CH_2OH$ | $(CH_3)_2N(CH_2CH_2OH)$ | 0.52 | stable |
| 4 | —$CH_2CH_2OH$ | —$CH_2CH_2OH$ | $N(CH_2CH_2OH)_3$ | 0.50 | separation |
| 5 | —$CH_2CH_2OH$ | —$CH_2CH_2OH$ | $(CH_3)_2N(CH_2CH_2OH)$ | 0.45 | stable |

The invention claimed is:

1. A composition comprising:
   i) at least one compound of formula (I) $N_1R_2R_3$ wherein $R_1$ and $R_2$, independently of each other, are selected in the group consisting of $C_1$-$C_3$ alkyl groups, and $R_3$ is a hydroxyethyl group; and
   ii) at least one compound selected in the group consisting of the following compounds of formula (IIb), (IIc) (IIe)

formula (IIb)

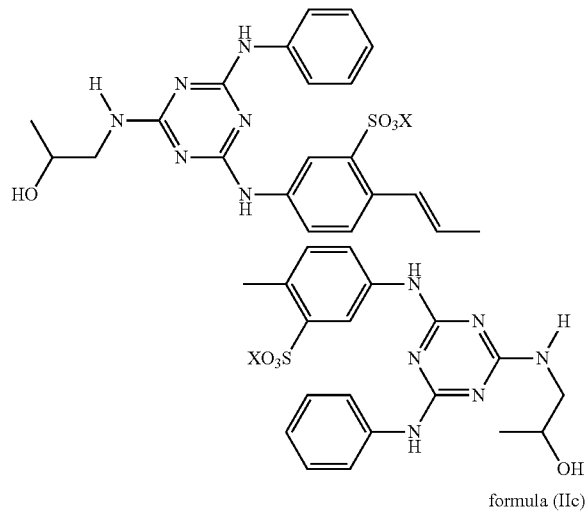

formula (IIc)

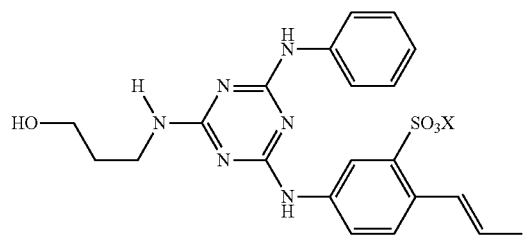

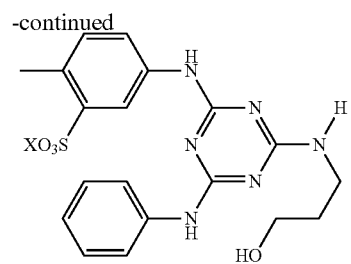

Formula (IIe)

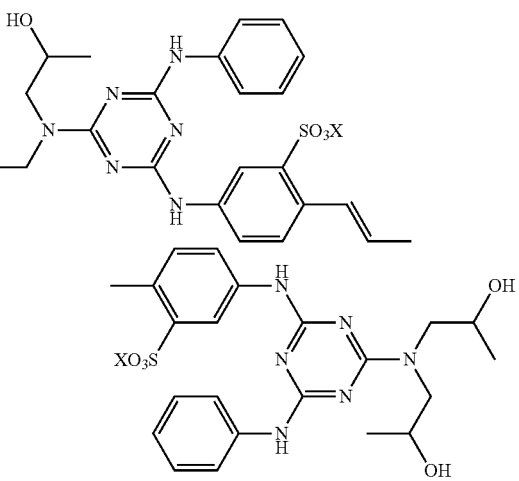

wherein
X is selected in the group consisting of hydrogen, alkaline metals, alkaline-earth metals, ammonium or ammonium derived from a compound of formula (I).

2. Composition according to claim 1, wherein said compound of formula (I) is 2-(dimethylamino)ethanol.

3. Compound of formula (III) selected in the group consisting of the compounds having the following formulas (IIIb), (IIIc), (IIIe):

formula (IIb)

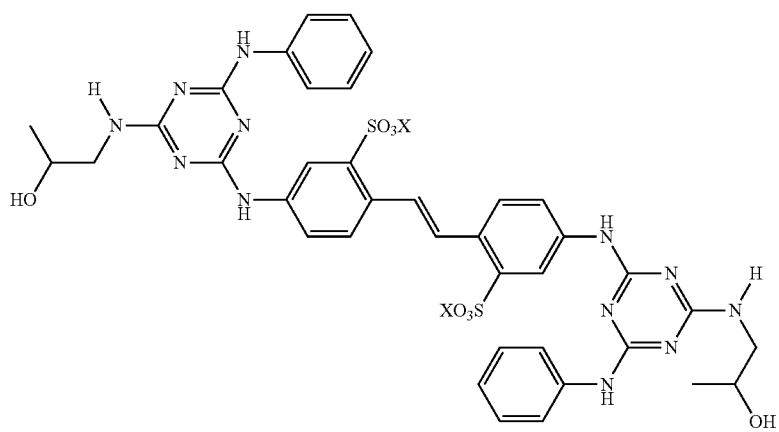

-continued
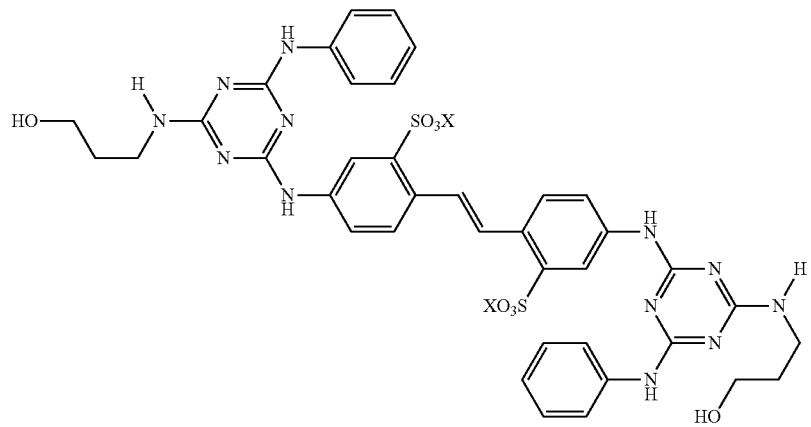
formula (IIc)
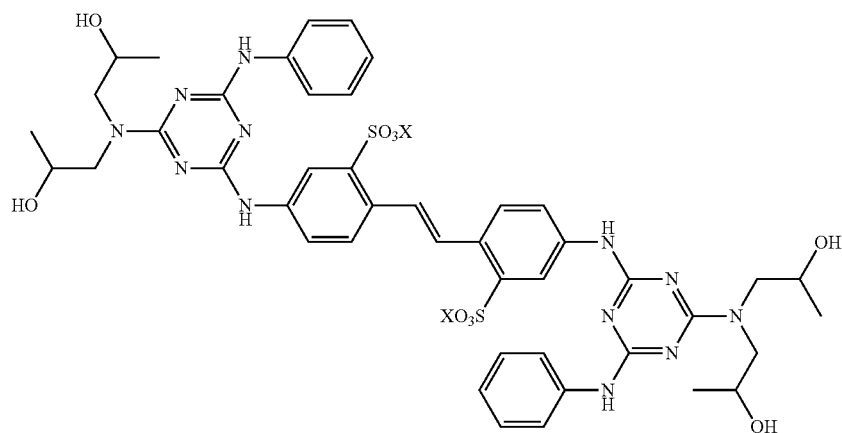
Formula (IIe)
wherein X' is an ammonium ion derived from a compound of formula (I) defined in claim 1.
4. Compound of formula (III) according to claim 3, wherein X' is an ammonium ion derived from 2-(dimethylamino)ethanol.
5. Process for preparing a compound according to claim 3, comprising the steps of:
mixing a compound of formula (IIb), (IIc) (IIe)
formula (IIIb)
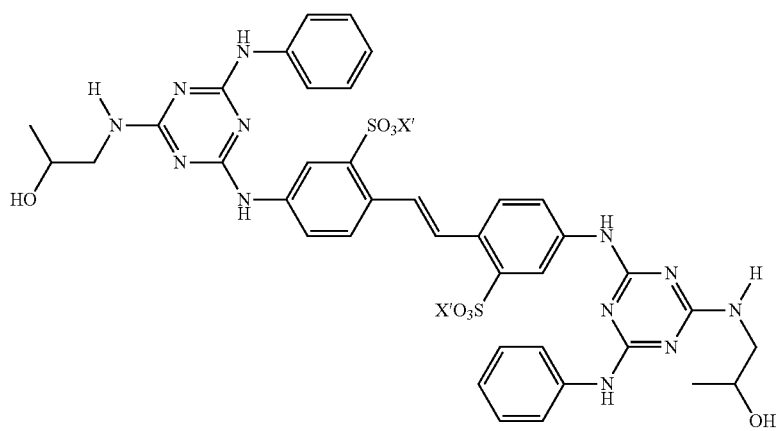

-continued

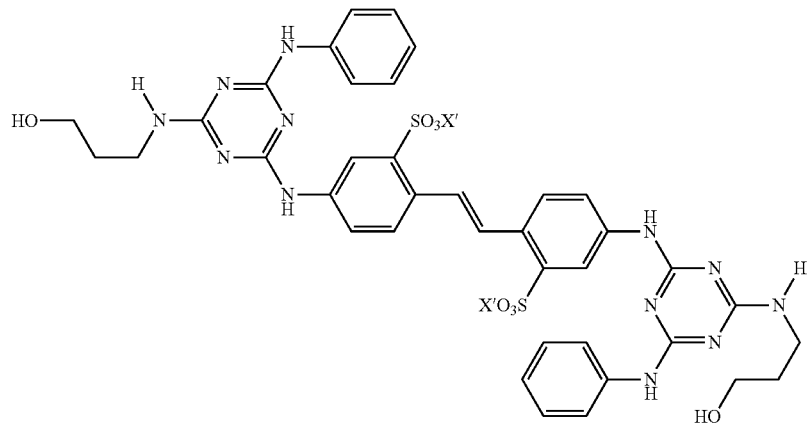

formula (IIIc)

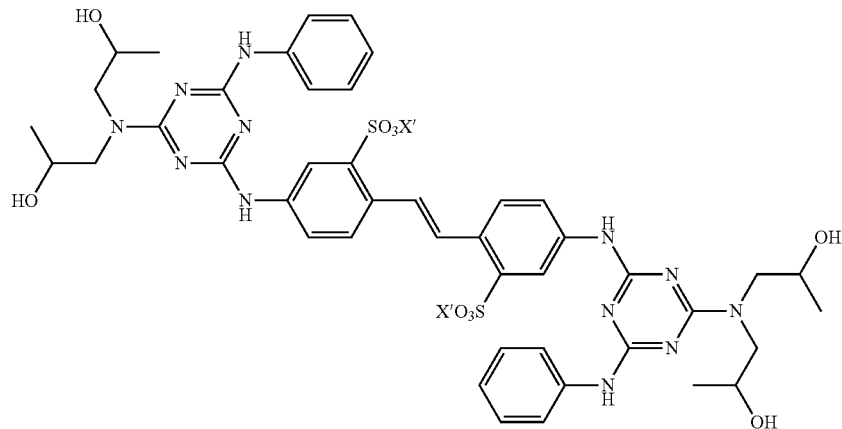

formula (IIIe)

wherein X is selected in the group consisting of hydrogen, alkaline metals, alkaline-earth metals, ammonium or ammonium derived from a compound of formula (I) with a compound of formula (I) $NR_1R_2R_3$ wherein $R_1$ and $R_2$, independently of each other, are selected in the group consisting of $C_1$-$C_3$ alkyl groups and $R_3$ is a hydroxyethyl group in a suitable solvent medium; and reacting at a temperature between 20° C. and 100° C.

6. Aqueous solution comprising:
3 to 20% by weight of at least one compound of formula (I) defined in claim 1 or mixtures thereof;
6 to 40% by weight of at least one compound of formula (Ib), (IIc), (IIe), (IIf) defined in claim 1 or mixtures thereof;
50 to 90% by weight of water and
0 to 1% by weight of additives.

7. Method of whitening paper with an aqueous solution according to claim 6, said method comprising:
adding said aqueous solution to a dispersion of fibers, or through size-press or through coating surface treatment; thereby obtaining said whitening of said paper.

8. Method according to claim 7 in the whitening treatment of natural, semisynthetic or synthetic fibres.

9. Compositions according to claim 1 wherein the ratio between the quantity in moles of said compound of formula (I) and said compounds of formula (IIb), (IIc), (IIe), (IIf) is less than 3.

* * * * *